(12) United States Patent
Langan et al.

(10) Patent No.: US 9,895,119 B2
(45) Date of Patent: Feb. 20, 2018

(54) GENERATION OF MASK AND CONTRAST IMAGE DATA IN A CONTINUOUS ACQUISITION

(71) Applicant: GENERAL ELECTRIC COMPANY, Schenectady, NY (US)

(72) Inventors: David Allen Langan, Clifton Park, NY (US); Bernhard Erich Hermann Claus, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 460 days.

(21) Appl. No.: 14/448,842

(22) Filed: Jul. 31, 2014

(65) Prior Publication Data

US 2016/0029987 A1 Feb. 4, 2016

(51) Int. Cl.
*A61B 6/00* (2006.01)
*A61B 6/03* (2006.01)
*A61B 6/02* (2006.01)

(52) U.S. Cl.
CPC .............. *A61B 6/486* (2013.01); *A61B 6/025* (2013.01); *A61B 6/032* (2013.01); *A61B 6/4014* (2013.01); *A61B 6/481* (2013.01); *A61B 6/5205* (2013.01); *A61B 6/504* (2013.01)

(58) Field of Classification Search
CPC ................................. A61B 6/481; A61B 6/504
See application file for complete search history.

(56) References Cited

U.S. PATENT DOCUMENTS

| 7,519,414 | B2 | 4/2009 | Mitschke et al. |
| 8,213,569 | B2 | 7/2012 | Zaiki et al. |
| 8,285,021 | B2 | 10/2012 | Boese et al. |
| 8,553,963 | B2 | 10/2013 | Rauch et al. |
| 8,654,119 | B2 | 2/2014 | Mistretta et al. |
| 2008/0247503 | A1 | 10/2008 | Lauritsch et al. |
| 2010/0215237 | A1* | 8/2010 | Ohishi .................. A61B 6/507 382/131 |
| 2013/0188771 | A1 | 7/2013 | Kyriakou |
| 2013/0190615 | A1 | 7/2013 | Royalty et al. |

FOREIGN PATENT DOCUMENTS

DE   102011083685 A1   4/2013

OTHER PUBLICATIONS

Martin Groher, "2D-3D Registration of Vascular Images Towards 3D-Guided Catheter Interventions", PhD Thesis Techinical University of Munich, 2008.

(Continued)

*Primary Examiner* — Dani Fox
(74) *Attorney, Agent, or Firm* — Pabitra K. Chakrabarti

(57) ABSTRACT

The present disclosure relates various approaches by which mask and contrast projection data may be acquired using a continuous projection acquisition process, without an interruption in acquisition or resetting of the system between the acquisition of the mask projection data and the contrast projection data. In certain implementations, the approaches described herein may be employed with a single-plane or multi-plane tomosynthesis system.

11 Claims, 6 Drawing Sheets

(56) References Cited

OTHER PUBLICATIONS

C A Mistretta, "The Development of Modern Angiographic Imaging; Application of Undersampled Acquisition and Constrained Reconstruction in the Post-Nyquist Era", Medical Physics International Journal, pp. 1, vol. 1, 2013.
Sawada, Hiroshi, et al.; "3D-DSA Application 'NaviDAS'"; Technical Report from the Medical Systems Division of the Shimadzu Corporation; 2 pages.
GE Healthcare; "Premium Digital Mobile Imaging System", 2008, pp. 1-16.
Philips Healthcare; "Advanced Interventions in Your Lab", 2009, pp. 1-28.
Non-Final Office Action dated Dec. 15, 2016, in related U.S. Appl. No. 14/602,051, pp. 1-17.
Final Office Action dated May 19, 2017, in related U.S. Appl. No. 14/602,051, pp. 1-20.

* cited by examiner

GENERATION OF MASK AND CONTRAST IMAGE DATA IN A CONTINUOUS ACQUISITION

BACKGROUND

The subject matter disclosed herein relates to contrast-enhanced imaging techniques and, more particularly, to the acquisition of both contrast-enhanced and mask image data over a continuous acquisition.

Non-invasive imaging technologies allow images of the internal structures of a patient or object to be obtained using various radiological principles that do not necessitate that an invasive procedure be performed on the patient or object. In particular, technologies such as X-ray fluoroscopy, X-ray computed tomography (CT), and tomosynthesis use various physical principles, such as the varying transmission of X-rays through a target volume, to acquire projection data and to construct images (e.g., three-dimensional, volumetric representations of the interior of the human body or of other imaged structures). However, the use of image-enhancing agents, such as contrast agents, may result in a discontinuous image acquisition process.

For example, in certain instances where contrast agents are employed, such as vascular imaging contexts, two distinct types of data may be acquired of the patient, a contrast-enhanced set of data and a set of mask data that is not contrast enhanced. Differential comparison of these two types of data may be employed to allow useful diagnostic information to be obtained. However, in certain circumstances, acquisition of the two types of data may need to occur under tight time constraints, which may lead to inefficiencies acquiring quality data, interruptions (i.e., discontinuities) in the data acquisition process, or a lengthier image acquisition session than may be desired. For example, in C-arm spin-type data acquisitions, a pause (i.e., dead time) occurs between spins (i.e., acquisitions) as the C-arm is repositioned to its start point, thereby lengthening the acquisition process as well as adding a temporal discontinuity in the acquired data.

BRIEF DESCRIPTION

In one embodiment, an imaging method is provided. In accordance with this method, an X-ray source and an X-ray detector of a tomographic imaging system are continuously moved in a periodic motion along a limited angular range with respect to an imaged volume. Each period of motion comprises an orbit of the X-ray source and the X-ray detector with respect to the imaged volume. A first projection dataset is acquired using the X-ray source and the X-ray detector. While the X-ray source and the X-ray detector continue to move after acquisition of the first projection dataset, a second projection dataset is acquired. At least one 3D subtracted image is reconstructed using the first projection dataset and the second projection dataset.

In a further embodiment, a contrast-enhanced imaging method is provided. In accordance with this method, a first imager, comprising a first X-ray source and a first X-ray detector, of a bi-plane tomographic imaging system is continuously moved in a first periodic motion along a first limited angular range with respect to an imaged volume. Each period of motion comprises an orbit of the first imager with respect to the imaged volume. A contrast agent is administered during the continuous motion of the first imager. A mask projection dataset is acquired using one or both of the first imager or a second imager prior to administering the contrast agent. A contrast projection dataset is acquired using one or both of the first imager or the second imager at the same time as or subsequent to starting to administer the contrast agent. A contrast-enhanced volume is reconstructed using the mask projection dataset and the contrast projection dataset.

In an additional embodiment, a contrast-enhanced imaging method is provided. In accordance with this method, a set of mask projection data is acquired using a first X-ray source and a first X-ray detector moving over a limited angular range relative to one side of an imaging volume. The first X-ray source and the first X-ray detector are not rotated around the imaging volume when moved over the limited angular range. A contrast agent is administered while continuing to move the first X-ray source and the first X-ray detector over the limited angular range. After administering the contrast agent and while continuing to move the first X-ray source and the first X-ray detector over the limited angular range, a set of contrast projection data is acquired using the first X-ray source and the first X-ray detector.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

In certain interventional or surgical procedures, it is useful to be able to visualize the internal structures of a patient as part of the procedure. For example, during interventional catheterization procedures, it is common to visualize vascular structures under X-ray by delivering (e.g., injecting) an iodinated contrast bolus into the vasculature of interest. The visualization of the imaged vasculature may be used for navigation and/or lesion assessment. In conventional approaches, the imaged vasculature often does not possess sufficient contrast to be adequately visualized in the context of surrounding physiological structures, thus motivating the use of approaches such as digital subtraction angiography (DSA). As discussed in greater detail below, the present approaches facilitate the acquisition and use of contrast-enhanced images, which may in turn be used in DSA or other procedures where contrast-enhanced images are useful.

Figure 1:
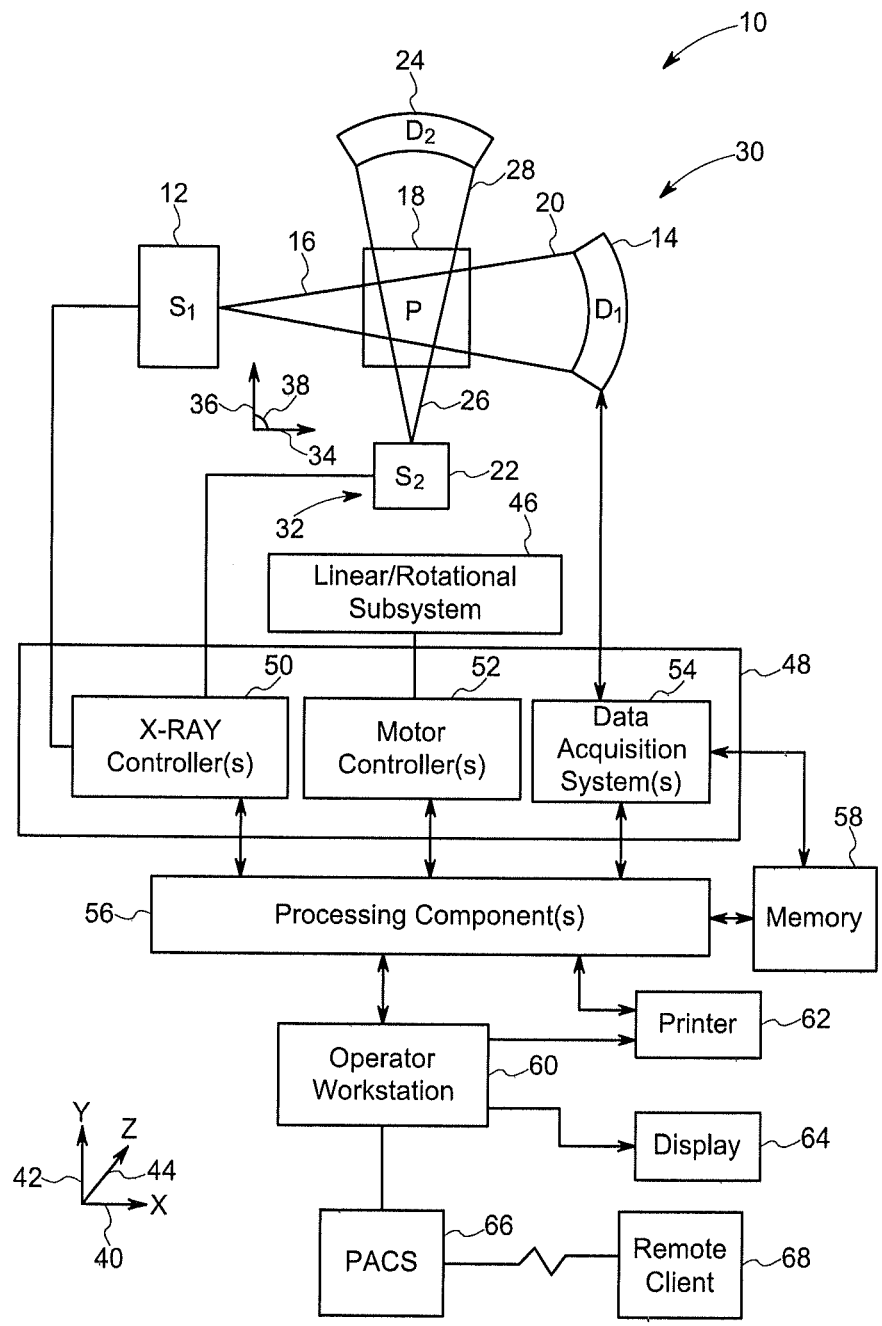
FIG. 1 is a diagrammatical view of an imaging system for use in producing images in accordance with aspects of the present disclosure.

With the preceding in mind, an example of a bi-plane tomosynthesis imaging system 10 designed to acquire X-ray attenuation data at a variety of views around a patient and suitable for tomographic imaging is provided in FIG. 1. In the embodiment illustrated in FIG. 1, imaging system 10 includes a first source of X-ray radiation 12 and a first detector 14. The first X-ray source 12 may be an X-ray tube, a distributed X-ray source (such as a solid-state or thermionic X-ray source) or any other source of X-ray radiation suitable for the acquisition of medical or other images.

The X-rays 16 generated by the first source 12 pass into a region in which a patient 18, is positioned. In the depicted example, the X-rays 16 are collimated to be a cone-shaped beam, e.g., a cone-beam, which passes through the imaged volume. A portion of the X-ray radiation 20 passes through or around the patient 18 (or other subject of interest) and impacts a detector array, represented generally as the first detector 14. Detector elements of the first detector 14 produce electrical signals that represent the intensity of the incident X-rays 20. These signals are acquired and processed to reconstruct images of the features within the patient 18.

In the depicted example, the bi-plane imaging system 10 includes a second source 22 of X-ray radiation and a second detector 24, which, like the first detector 14, may include an array of detector elements. The second source 22 also generates X-rays 26, which may be collimated to form any suitable shape (e.g., a cone). The X-rays 26 are partially attenuated such that a portion 28 passes through the patient 18 and impacts the second detector 24. The second detector 24 generates electrical signals, which are acquired and processed to reconstruct images of the features within the patient 18. Though the depicted tomosynthesis system 10 depicts two separate imaging subsystems (i.e., a first source and detector and a second source and detector), it should be understood that this illustration is merely for completeness and is only one example of a suitable system for implementing the present approaches. Indeed, the present approach may also be employed with a tomosynthesis system having only a single imaging subsystem (i.e., a single-plane system) or having more than two such imaging subsystems (i.e., bi-plane or multi-plane).

In the present example, the first source 12 and first detector 14 may be a part of a first imager 30. The first imager 30 may acquire X-ray images or X-ray projection data over a limited angular range with respect to one side or facing (e.g., the anterior/posterior (AP) direction) of the patient 18, thereby defining data in a first plane (e.g., a frontal plane of the patient 18). The second source 22 and the second detector 24, if present and employed, may be a part of a second imager 32. The second imager 32 may acquire data within a different limited angular range with respect to a different side or facing (e.g., a lateral direction) of the patient 18, thereby defining data in a second plane (e.g., a lateral plane of the patient 18). In this context, an imaging plane may be defined as a set of projection directions that are located within a certain angular range relative to a reference direction. For example, the frontal imaging plane may be used to describe projection views within an angular range that is within, for example, 60 degrees of the PA (posterior/anterior) direction of the patient. Similarly, the lateral imaging plane may be described as the set of projection directions within an angular range that is within 60 degrees of the lateral/horizontal left/right projection direction. A variety of configurations may be employed where the first and second imagers 30, 32 obtain data that may be jointly used to construct and/or update one or more three-dimensional images of the patient 18 (e.g., tissues of interest of the patient 18).

As depicted, the first imager 30 positions the first source 12 and the first detector 14, at rest, generally along a first direction 34, which may correspond to the AP direction of the patient 18 in certain embodiments. The second imager 32 positions the second source 22 and the second detector 24, at rest, generally along a second direction 36, which may correspond to the lateral direction of the patient 18 in certain embodiments. The first and second directions 34, 36 may be oriented at an angle 38 relative to one another. The angle 38 may be any angle that is suitable to enable the first and second imagers 30, 32 to acquire projection data over separate and distinct limited angular ranges with respect to the patient. Further, the angle 38 may be adjusted by various features of the system 10, such as various linear and rotational systems or, in other embodiments, by an operator. Generally, the angle 38 may be between 30 and 180 degrees, but it may be desirable in certain embodiments for the first and second imagers 30, 32 to be oriented crosswise relative to one another, such as between 30 and 90 degrees, or between 90 and 150 degrees. In one embodiment, the angle 38 is approximately 90 degrees.

In accordance with present embodiments, the first imager and the second imager 30, 32 may be moved relative to the patient or imaged object and relative to one another along one or more axes during an examination procedure during which projection data is acquired. For example, the first imager 30 may move about a first axis of rotation 40, a second axis of rotation 42, or a third axis of rotation 44, or any combination thereof, and the second imager 32 may move about any one or a combination of these axes as well. In one embodiment, the rotation of the first and second imagers 30, 32 may be coordinated in accordance with a specified protocol. In a further implementation, the second imager 32 may be stationary and may, therefore, only acquire projection data from a fixed position relative to the first imager 30.

The movement of the first imager 30 and/or the second imager 32 may be initiated and/or controlled by one or more linear/rotational subsystems 46. The linear/rotational subsystems 46, as discussed in further detail below, may include support structures, motors, gears, bearings, and the like, that enable the rotational and/or translational movement of the imagers 30, 32. In one embodiment, the linear/rotational subsystems 46 may include a first structural apparatus (e.g., a C-arm apparatus having rotational movement about at least two axes) supporting the first source and detector 12, 14, and a second structural apparatus (e.g., a C-arm apparatus) supporting the second source and detector 22, 24.

A system controller 48 may govern the linear/rotational subsystems 46 that initiate and/or control the movement of the first and second imagers 30, 32. In practice, the system controller 48 may incorporate one or more processing devices that include or communicate with tangible, non-transitory, machine readable media collectively storing instructions executable by the one or more processors to perform the operations described herein. The system controller 48 may also include features that control the timing of the activation of the first and second sources 12, 22, for example, to control the acquisition of X-ray attenuation data obtained during a particular imaging sequence. The system controller 48 may also execute various signal processing and filtration functions, such as for initial adjustment of dynamic ranges, interleaving of digital projection data, and so forth. Therefore, in general, the system controller 48 may be considered to command operation of the imaging system 10 to execute examination protocols. It should be noted that, to facilitate discussion, reference is made below to the system controller 48 as being the unit that controls acquisitions, movements, and so forth, using the imagers. However, embodiments where the system controller 48 acts in conjunction with other control devices (e.g., other control circuitry local to the imagers or remote to the system 10) are also encompassed by the present disclosure.

In the present context, the system controller 48 includes signal processing circuitry and various other circuitry that enables the system controller 48 to control the operation of the first and second imagers 30, 32 and the linear/rotational subsystems 46. In the illustrated embodiment, the circuitry may include an X-ray controller 50 configured to operate the first and second X-ray sources 12 and 22 so as to time the operations of these sources and to interleave the acquisition of X-ray attenuation data when needed. Circuitry of the system controller 48 may also include one or more motor controllers 52. The motor controllers 52 may control the activation of various components that are responsible for moving the first and second sources 12, 22 and the first and second detectors 14, 24. For example, the motor controllers 52 may coordinate movement of the first and second imagers 30, 32 such that the imagers obtain data from different projection directions, maintain a desired degree of angular separation, and also for collision avoidance. In other words, the motor controllers may implement a particular trajectory for each of the first and second imagers 30, 32.

The system controller 48 is also illustrated as including one or more data acquisition systems 54. Generally, the first and second detectors 14, 24 may be coupled to the system controller 48, and more particularly to the data acquisition systems 54. The data acquisition systems 54 may receive data collected by read out electronics of the first and second detectors 14, 24, and in certain embodiments may process the data (e.g., by converting analog to digital signals or to perform other filtering, transformation, or similar operations).

It should be noted that the tangible, non-transitory, machine-readable media and the processors that are configured to perform the instructions stored on this media that are present in the system 10 may be shared between the various components of the system controller 48 or other components of the system 10. For instance, as illustrated, the X-ray controller 50, the motor controller 52, and the data acquisition systems 54 may share one or more processing components 56 that are each specifically configured to cooperate with one or more memory devices 58 storing instructions that, when executed by the processing components 56, perform the image acquisition techniques described herein. Further, the processing components 56 and the memory components 58 may coordinate in order to perform various image reconstruction processes.

The system controller 48 and the various circuitry that it includes, as well as the processing and memory components 56, 58, may be accessed or otherwise controlled by an operator via an operator workstation 60. The operator workstation 60 may include any application-specific or general-purpose computer that may include one or more programs (for example one or more imaging programs) capable of enabling operator input for the techniques described herein. The operator workstation 60 may include various input devices such as a mouse, a keyboard, a trackball, or any other similar feature that enables the operator to interact with the computer. The operator workstation 60 may enable the operator to control various imaging parameters, for example, by adjusting certain instructions stored on the memory devices 58.

The operator workstation 60 may be communicatively coupled to a printer 62 for printing images, patient data, and the like. The operator workstation 60 may also be in communication with a display 64 that enables the operator to view various parameters in real time, to view images produced by the acquired data, and the like. The operator workstation 60 may also, in certain embodiments, be communicatively coupled to a picture archiving and communication system (PACS) 66. Such a system may enable the storage of patient data, patient images, image acquisition parameters, and the like. This stored information may be shared throughout the imaging facility and may also be shared with other facilities, for example, a remote client 68. The remote client 68 may include hospitals, doctors' offices, or any other similar client.

Figure 2:
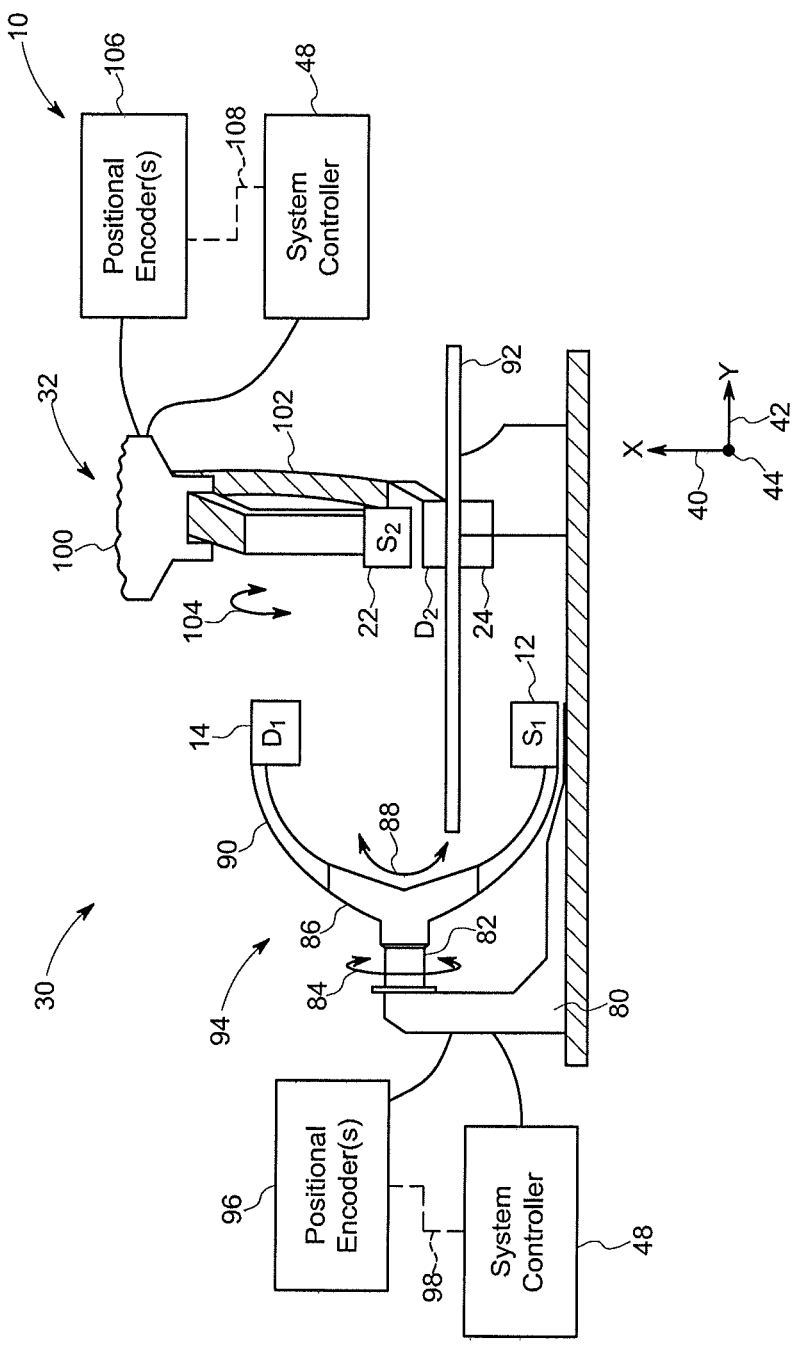
FIG. 2 is a schematic side view of a bi-plane imaging system in which a first imaging apparatus and a second imaging apparatus each obtain projection data along a plane, and the first imaging apparatus obtains projection data via rotation about two axes, in accordance with aspects of the present disclosure.

Various aspects of the present approaches may be further appreciated with respect to FIG. 2, which is a side view of an embodiment of the system 10. As illustrated, the system 10 includes the first imager 30 and the second imager 32. It should be noted that in practice, the second imager 32 may actually be closer in space to the first imager 30 than as illustrated in FIG. 2 (e.g., moved to the left in the illustration). However, to facilitate discussion of the present techniques and for clarity, the second imager 32 is depicted as being positioned further away from where it would, in practice, image the patient 18. The first imager 30, as illustrated, includes a first base 80 and a rotatable extension 82 extending from the first base 80. In the illustrated embodiment, the first base 80 is a floor-mounted base such that the first imager 30 may be secured to a floor of an imaging area in which it is positioned. In other embodiments, however, the first base 80 may not be secured to the floor (e.g., may be movable, or may be mounted to the ceiling, etc.).

The rotatable extension 82 is depicted as extending generally along the second axis of rotation 42, and enables the first source 12 and the first detector 14 to move about the second axis of rotation 42. For example, the rotatable extension 82 may enable the first source 12 and the first detector 14 to move about the second axis of rotation 42 in a manner that maintains their position relative to one another throughout the rotation. The rotation enabled by the rotatable extension 82 is shown as double-headed arrow 84. The rotatable extension 82 is coupled to a first moving structure 86 (e.g., directly or indirectly via an extension arm), which enables the first source 12 and the first detector 14 to move about the third axis of rotation 44. This rotation about the third axis of rotation 44 is depicted as double-headed arrow 88.

The first moving structure 86 may be a geared or track structure that is motively coupled to a first support structure 90 that physically supports the first source 12 and the first detector 14, and may be in the form of a C-arm, or any other shape that positions the first source 12 and the first detector 14 on either side of the patient 18. As illustrated, the first support structure 90 includes an arcuate structure that extends from a first side of a patient table 92, around the patient table 92, and to a second side of the patient table 92. In this way, the first source 12 and the first detector 14 generally remain positioned at opposite ends and/or on opposite sides of the patient (not shown) positioned on patient table 92. Together, the first base 80, the rotatable extension 82, the first moving structure 86, and the first support structure 90 may be considered to be the first structure 94 of the first imager 30.

The first imager 30 may include various motors, actuators, or other features responsible for movement of the various structures of the first imager 30, and they may be communicatively coupled to one or more positional encoders 96. The one or more positional encoders 96 may encode the respective positions of any one or more components of the first imager 30 in a manner that facilitates processing by the system controller 48. In such an implementation, the positional encoders 96 may provide feedback 98 (for example via wired or wireless signals) to the system controller 48. The system controller 48 may use this feedback 98 to control either or both the first imager 30 and the second imager 32.

In the illustrated embodiment, the second imager 32 is depicted as including a second base 100. The second base 100 may be mounted to any structure, or may be a mobile base. However, in the illustrated embodiment, the second base 100 is depicted as a ceiling-mounted structure. The second base 100 may also include various motive devices such as gears, actuators, tracks, or any similar features that enable movement of the second source 22 and the second detector 24. Specifically, the second base 100 is physically and motively coupled to a second support structure 102, which is depicted as a curved structure that suspends the second source 22 and the second detector 24 on opposite sides or ends of the patient table 92 (e.g., along a lateral direction of the patient 18). The motive devices or similar features of the second imager 32 may operate to move the second source 22 and the second detector 24 about the patient table 92 in one or more rotational directions.

In one embodiment, the second source 22 and the second detector 24 may move about the second axis of rotation 42 or another axis of rotation. The rotation by the second imager 32 is depicted as double-headed arrow 104. In some embodiments, the data acquired with the second imager 32 is used as a partial set of data that is used to reconstruct a 3D volume. Obtaining data along the additional trajectory traversed by the second imager 32 may be desirable to obtain data that can be useful in reconstructing three-dimensional images from incomplete data sets acquired using the first imager 30.

Like the first imager 30, the second imager 32 is depicted as being communicatively coupled (for example via wired or wireless communication) to one or more positional encoders 106, which may be shared with the first imager 30 or may be entirely separate from the first imager 30. The positional encoders 106 may encode the position of any one or more of the second base 100, the second support structure 102, the second detector 22 or the second detector 24, or any other feature of the second imager 32. The positional encoder 106 may provide feedback 108 to the system controller 48 to enable the system controller 48 to determine the position of the features of the second imager 32 relative to the features of the first imager 30, or relative to any other appropriate reference (e.g., a three-dimensional space established by one or more devices that provide and/or control position information of system components and/or devices).

As an example, the system controller 48 may simultaneously move the first source 12 and the first detector 14 together about the first axis of rotation 40, the second axis of rotation 42, or the third axis of rotation 44, or any combination thereof, and obtain first X-ray attenuation data for a subset of the traversed view angles. At substantially the same time, the system controller 48 may simultaneously move the second source 22 and the second detector 24 together about the first, second, or third axes of rotation 40, 42, 44, or any combination thereof, in order to obtain second X-ray attenuation data for one or more of the traversed view angles. In one embodiment, the system controller 48 may receive positional information from the positional encoders 96, 106, relating to the first imager 30 and the second imager 32, and may calculate a trajectory (or update a modeled trajectory) for either or for both of the first source and detector 12, 14 and the second source and detector 22, 24 using this positional feedback information.

Furthermore, the system controller 48 may synthesize one or more volumetric images using data obtained by the first imager 30 and the second imager 32. For example, in one embodiment, projection images/data obtained by the second imager 32 may be used to supplement the data obtained by the first imager 30 for reconstruction of a 3D image. In such an embodiment, the first imager 30 may perform a first acquisition of data using a first trajectory (e.g., a circular, ellipsoidal, or similar path traced by the first source 12 below the patient 18 and a corresponding circular, ellipsoidal, or similar path traced by the first detector above the patient 18, referred to herein as a frontal tomosynthesis trajectory). In this example, the first imager 30 may obtain projection data from a plurality of projection directions, but these projection directions may be limited by the angular range of motion of the first imager 30 (e.g., the limited angular displacement about the second rotational axis 42) and/or the presence of structures associated with the second imager 32, or other devices or structures. In one embodiment, the angular range of the trajectory may also be limited due to temporal constraints. In one example, the angular range of an elliptical orbit that is part of the trajectory may be defined by the requirement that the orbit may have to be traversed in a certain amount of time, e.g., in 3 seconds or less. In accordance with certain embodiments, the second imager 32 may move about the second rotational axis 42 at projection directions beyond those obtained by the first imager 30 (e.g., at larger angles relative to the frontal plane of the patient 18). Thus, the data obtained by the second imager 32 may complement the data obtained by the first imager 30, and may enable the system controller 48 (or other reconstruction device) to perform 3D tomosynthesis reconstruction using a more complete set of data. This data may be considered to be obtained by the second imager 32 via lateral plane imaging, in that the second X-ray source 22 may generate a trajectory that may trace a line or non-linear path along a lateral direction of the patient 18 (and at angular displacements therefrom). Various tomosynthesis reconstruction algorithms that may be used to reconstruct a 3D volumetric image of the imaged region of interest include those that are well known by those of ordinary skill in the art, and may be of the analytical or iterative type, including but not limited to filtered back projection. In certain embodiments, data acquisition by the first and second imagers 30, 32 may be interleaved in order to avoid signal contamination between the imagers.

With the preceding in mind, as used herein, a tomosynthesis trajectory of an imager may be described as a path (e.g., a line, curve, circle, oval, and so forth, as well as combinations thereof) traced by an X-ray source during image acquisition. A tomosynthesis acquisition by an imager or imager subsystem occurs over a limited angular range with respect to the patient (such as with respect to one side, e.g., the front back, left side, or right side, of the patient), and thus a trajectory will typically move the source within this limited angular range with respect to the imaged subject. Such trajectories may be periodic in that the path traced by the X-ray source may be repeated throughout the examination. As used herein, each period of motion may be referred to as an orbit. For example, in the context of an oval or circular trajectory, an endpoint of one orbit may correspond to the beginning point of the next orbit. Similarly, linear or non-linear paths traced by the X-ray source may be repeated in a back-and-forth manner, leading to a periodic type trajectory. For example, an X-ray source may be moved (i.e., have a trajectory) in a circular or oval periodic motion (e.g., an orbit) in front of the patient, without rotating around the patient, thereby acquiring X-ray projection data over a limited angular range with respect to the patient. Such a motion is in contrast to the spin-type source motion or trajectory typically associated with computed tomography (CT) type systems and acquisitions.

In certain embodiments, a trajectory of an imager may include segments that allow, for example, for reaching a mechanical periodic steady state before data acquisition starts. Such a periodic steady state may be characterized as repeatedly traversing a closed, smooth curve, resulting in a smooth periodic motion (where each segment representing a complete traversal of the closed curve may be referred to as an orbit). In one embodiment, the closed curve is traversed at least two times, i.e., the trajectory contains at least two full consecutive orbits. The trajectory may also include segments that are not part of the periodic motion, e.g., segments that are used to acquire additional data at view angles that are outside of the angular range represented by the closed curve. In one embodiment, data acquisition while the imager traverses the trajectory may be adapted to certain events. That is, the acquisition of a dataset may start at the point in time when the imager enters into periodic orbits. In another example, data acquisition may start after a fixed delay relative to the start of a contrast injection; or data acquisition may start at the start of a contrast injection, but with a lower frame rate. The frame rate may then be adjusted to the nominal frame rate, when a desired degree of opacification of the imaged structures due to the injected contrast medium is detected. Note that in this example the data acquisition only needs to be synchronized with the contrast injection. Synchronization requirements with the imager motion are minimal as long as the imager is in the periodic steady-state segment of the trajectory.

To further differentiate the present approach from conventional approaches employing a spin-type acquisition, a brief discussion of such a spin-type acquisition is provided. In such an acquisition, such as in conventional three-dimensional (3D) DSA, an interventional C-arm system or a computed tomography (CT) system is employed that utilizes a "spin acquisition" about the patient (i.e., the source and detector arrangement is rotated, at least partly (e.g., 200° to 360°), around the patient). The spin acquisition acquires projection data as the gantry rotates about the patient. A spin can take 3 to 20 seconds to acquire the data and a pause (or dead time) must be incurred before a spin can be repeated as the X-ray source is repositioned to its initial or start position to allow different spin acquisitions to be spatially registered with respect to the patient. This repositioning step is inflexible and imposes serious constraints on conventional spin acquisition processes.

Figure 3:
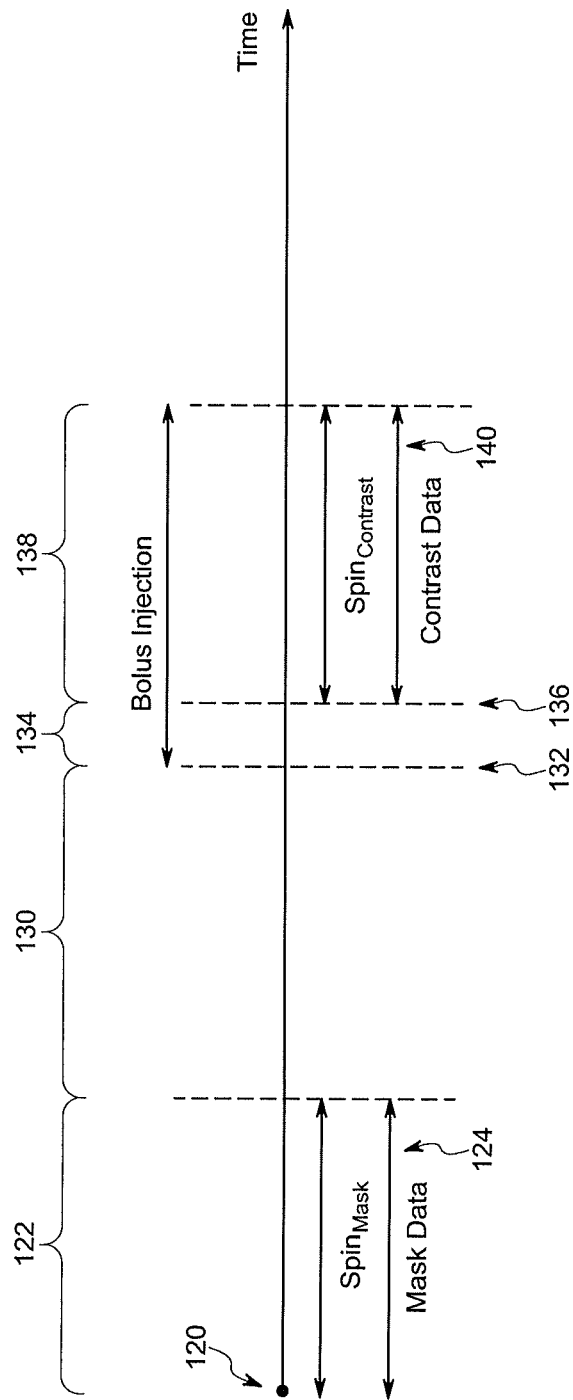
FIG. 3 is a timeline depicting a conventional spin-type data acquisition.

A timeline of one such acquisition can be seen in the context of FIG. 3. In this depicted example, the examination begins at $t_0$ 120, at which time the gantry motion begins, rotating an X-ray source and detector about the patient. The gantry spins for the duration of an initial spin 122, during which a set of mask data 124 is acquired. In the depicted example, the mask data 124 represents the data corresponding to one spin of the gantry while no contrast is present in the vasculature. After acquisition of the mask data 124, a time delay 130 is incurred during which data acquisition is stopped and the gantry (and, thus, the source and detector) are repositioned to their initial positions at $t_0$ 120 for the subsequent contrast data collection step. This constitutes "dead time" in the acquisition process during which data collection is not occurring, but during which the patient has to remain generally stationary. After the source and detector are returned to their initial position, the contrast bolus injection may be started at $t_1$ 132, after which there is a further time delay 134 during which the target vasculature is opacified to the desired degree by the injected contrast. As will be appreciated, contrast may continue throughout the acquisition of contrast image data, as described in greater detail below. Once the desired degree of opacification exists within the target vasculature, the gantry is put in motion once again at $t_2$ 136 to rotate the X-ray source and detector about the patient (i.e., additional or contrast spin 138), during which a set of contrast data 140 is acquired. In the depicted example, the contrast data 140 represents the data corresponding to the spin 138 of the gantry while the target vasculature is opacified by contrast.

The lack of a continuous, repeatable, acquisition (due to the incurred dead time 130, 134 between spins) creates several complications for such a 3D DSA application. For example, the increased temporal separation between the "mask" and "contrast" acquisitions (i.e., first spin 122 and second spin 138) increases the opportunity for patient motion, thereby potentially impairing subtracted image quality. In addition, the timing of the contrast bolus injection must be predetermined and precisely coordinated with the spin acquisition (spin 138) directed to acquisition of contrast data 140. Imaging temporal dynamics, perfusion or otherwise, may benefit from the acquisition of additional spin datasets after the contrast injection and may be impaired by the reduced and discontinuous temporal sampling. Lastly, coordination with physiological monitoring equipment, if employed, is complicated by the discontinuous nature of the spin acquisition process.

In contrast to this conventional approach, the present approach allows for continuous data acquisition throughout the examination. In particular, the present disclosure is generally directed to enabling the acquisition of mask and contrast projection data in a single continuous acquisition during an interventional X-ray procedure. The continuous gantry motion and data acquisition, as discussed herein, provides greater flexibility compared to prior approaches, including allowing flexibility with respect to when the contrast bolus is injected. The mask and contrast projection data may, in one embodiment, be used in a 3D DSA examination. The periodic part of the imager trajectory is presumed to be continuous and repeatable with a temporal period in the 2-10 second range, thereby allowing for acquisition of two or more datasets where a significant portion of the view angles are essentially identical between datasets.

In accordance with presently disclosed embodiments, the timing of the contrast bolus injection is not critical, though in certain embodiments it is withheld until at least one acquisition period (i.e., a mask acquisition), acquired during one orbit of the periodic part of the trajectory, has been performed. The contrast bolus is typically of sufficient quantity and duration to opacify the vasculature of interest for at least one acquisition period (i.e., for the time it takes to traverse one orbit). Physiologic monitoring equipment may be employed for use in coordination of the acquisition, administration of the contrast bolus, and/or the reconstruction processing.

Figure 4:
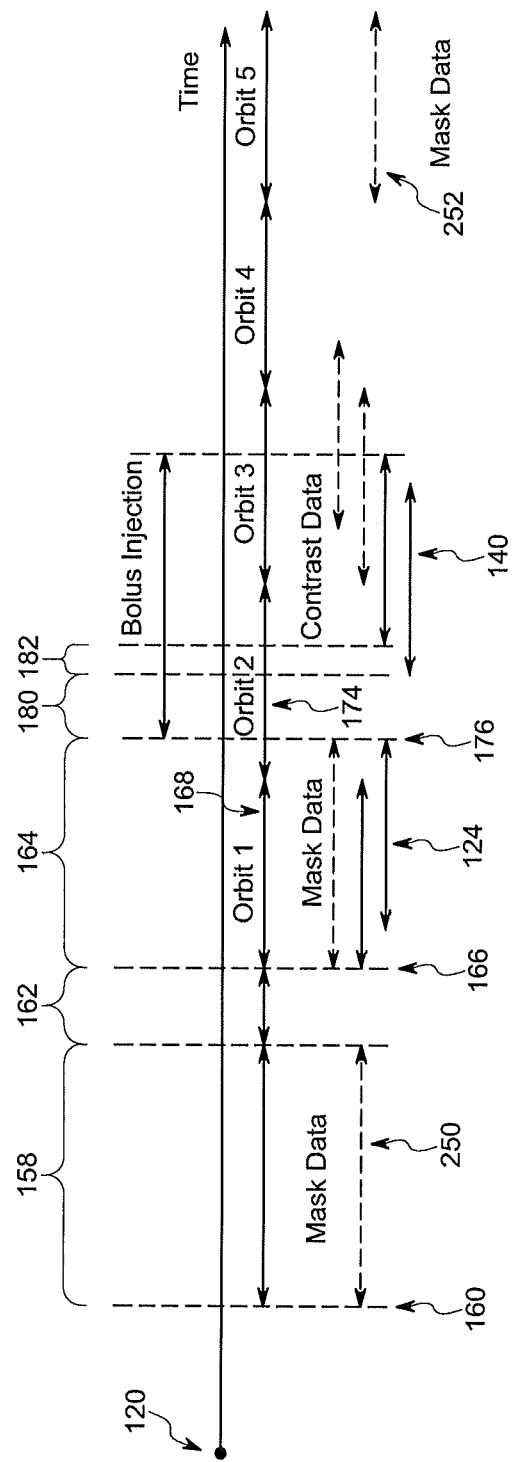
FIG. 4 is a timeline depicting a non-spin acquisition in accordance with aspects of the present disclosure.

By way of example, and turning to FIG. 4, a sample timeline is depicted in accordance with present embodiments. In this example, the C-arm (or other support and motion structure) may be initially put in motion and the examination started at $t_0$ 120. In the depicted example, the C-arm(s) may undergo an initial period where the motion of the C-arm or arms is initiated. During this initial phase there may also be an interval 158 during which the C-arm(s) may undergo motion that is different from what will be performed during the periodic motion phase, such as motions having an augmented or different geometry, including smaller or larger angular ranges or motion, smaller or larger orbits, and so forth. In certain implementations, the vibrations associated with start-up motion may diminish after a certain interval (e.g., as denoted as starting at time 160). In the depicted example a transition interval 162 is depicted during which the motion of the C-arm(s) then transitions to a prescribed periodic motion or trajectory. In the depicted example, periodic steady state-motion of the C-arm(s) begins at time 166. Motion of the C-arm(s) and supported X-ray source and detector is continuous during this time (i.e., the assembly is not stopped and repositioned).

When the periodic steady state-motion of the C-arm(s) begins at time 166, this may denote the beginning of a first orbit 168 of the system. Mask data 124 may be acquired (interval 164) for at least one orbit or by combining data from more than one orbit (if available), e.g., by appropriately averaging, as denoted by the dotted mask data line generated by averaging the two solid mask data lines for view angles where more than one projection is available. Note that using more than a single orbit worth of projection data results generally in higher quality mask data (e.g., through noise reduction due to averaging). Alternatively, the data selected as corresponding to the mask data 124 may be selected from the last full orbit prior to starting the administration 176 of the contrast bolus in order to minimize the time differential between acquisition of the mask data 124 and contrast data 140.

In one implementation, at the conclusion of the initial acquisition of mask data 124, a contrast bolus injection is started as step 176. In the depicted example, the contrast bolus is injected after the start of the second orbit 174. As noted above, the contrast bolus is injected without stopping or repositioning the source and detector components, and proceeds while these components are in motion and potentially, in operation. After starting the injection of the contrast at time 176, there is a delay during which the contrast is dispersed in the vasculature. In this example, the delay 180 may denote an interval during which opacification of the vasculature of interest is achieved. In one embodiment, no data is acquired during this interval. Once the desired degree of opacification is achieved (e.g., a fixed time after the start of the injection), contrast data 140 may be acquired, such as over the interval of one or more orbits (e.g., at least one full orbit) or by averaging the contrast data acquired over multiple orbits. It should be noted that in certain implementations, the X-ray source(s) may be controlled so as to only emit X-rays during the times when mask data 124 or contrast data 140 are being acquired, and not during those periods of time when no data is being acquired. For example, no data may be acquired during interval 162 (transition from initial phase to periodic motion), and interval 180 (time delay from start of bolus injection to full opacification of the vasculature). While the preceding example of an implementation describes mask data 124 as being acquired prior to contrast data 140, it should be appreciated that this order may be reversed, with the contrast data 140 being acquired first once steady state periodic motion is achieved and mask data 140 being acquired after the contrast is washed-out of the vasculature. In such a reversed scenario, data acquisition may still be performed in a continuous manner, without stopping or repositioning the source and detector components between the contrast and mask acquisitions. In one embodiment, mask data may be acquired before and after the contrast data acquisition, e.g., for averaging, of for selection of the mask dataset with the minimum registration error relative to the contrast dataset.

As will be appreciated in comparison to a spin-type acquisition, such as that depicted in FIG. 3, one advantage of the approach depicted in FIG. 4 is that there is no need to introduce a time delay during which a gantry or C-ram is returned to a start position to separately acquire the mask data 124 and contrast data 140. As a result, there is better alignment between the mask data 124 and contrast data 140 (i.e., reduced risk of patient motion, leading to better image quality in the subtracted datasets). Indeed, in certain implementations, the mask data 124 and contrast data 140 may be acquired in a single breath-hold. In addition, the orbit time (which occurs only over a limited angular range) for the approach shown in FIG. 4 may be less than time for spin. Thus, the amount of contrast employed i.e., the bolus may be less. Further, the tomosynthesis motion associated with the acquisitions of FIG. 4 (and the systems shown in FIGS. 1 and 2) is less intrusive within interventional suite. Lastly, due to the ongoing or continuous nature of the acquisition, there is more flexibility in terms of contrast administration (e.g., the contrast injection does not need to be synchronized with the gantry motion, only with the data acquisition) and so forth.

Figure 5:
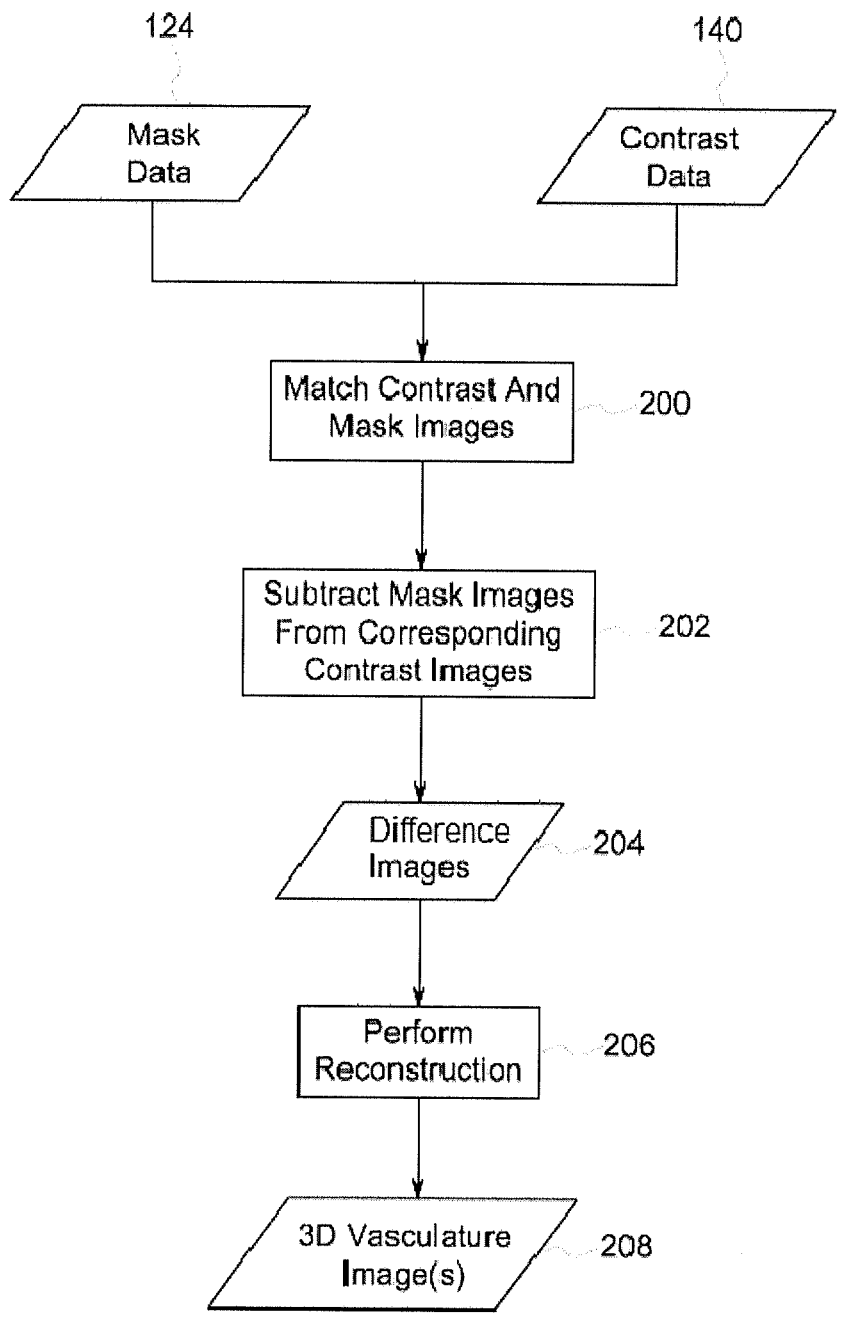
FIG. 5 is a process flow diagram describing steps for generating a three-dimensional image in accordance with aspects of the present disclosure.
Figure 6:
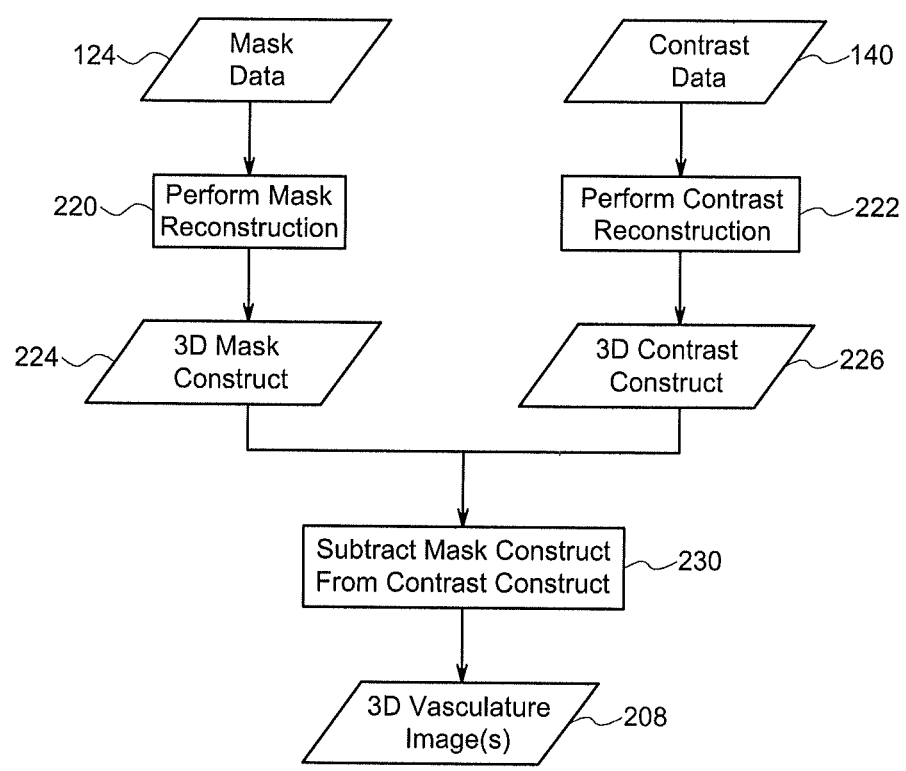
FIG. 6 is a process flow diagram describing alternative steps for generating a three-dimensional image in accordance with aspects of the present disclosure.

With the timeline of FIG. 4 in mind, and turning to the flow chart of FIG. 5, in one embodiment, for each image in a contrast sequence (i.e., contrast data 140), a corresponding image (i.e., an image acquired at the same view angle) is identified (block 200) in the mask sequence (i.e., mask data 124). The mask images are then subtracted (block 202) from the corresponding contrast images to generate a respective difference image 204 for each image in the sequence. The difference images may then be used in a 3D reconstruction algorithm (block 206) to generate a 3D vascular tree 208 for display. In another embodiment, instead of, or in addition to, the 3D vascular tree, the subtracted projection images are displayed. Alternatively, as shown in FIG. 6, the images of the mask data 124 and contrast data 140 may be separately reconstructed (blocks 220, 222 to generate a respective 3D mask construct 224 and contrast constructs 226. In such an implementation, the mask construct 224 may be subtracted (block 230) from the contrast construct 226 in the volume domain to generate the 3D vascular tree 208 for display. In one such embodiment, the mask data that is used for the reconstruction of the 3D mask image may comprise more data than the dataset corresponding to a single orbit. For example, it may include data from the second imager, as well as data corresponding to the augmented geometry, as discussed herein below. In yet another embodiment (not shown), the 3D mask volume may be reprojected to create synthetic mask projection images, and this synthetic mask data is then subtracted from the contrast data to create subtracted projection data, from which the 3D contrast volume can be reconstructed.

While the preceding describes one implementation of the present approach, this implementation may be extended to provide additional flexibility. For example, with FIG. 4 as a reference, in a first modification the acquisition window may be extended for the contrast imaging sequence to encompass more than one orbit. Such an extension enables selection or designation of a suitable time interval for contrast data 140 to be used for the 3D reconstruction (depicted by the two solid arrows spanning the second and third orbits) if the prior estimate of the delay until the target vessels were opacified was incorrect.

By way of example, in FIG. 4 the initial delay 180 allocated for vessel opacification may have been followed by contrast data collection beginning, as shown by the bottom solid arrow. However, once data acquisition begins, it may be observed that an additional delay 182 elapses before full opacification of the vessels is reached, and contrast data collection for a full orbit may occur from that point. That is, acquisition of the contrast data 140 may be extended beyond the duration of a single orbit to account for additional delays in the vessel opacification. Thus, in combination, contrast data collection may be performed for more than a full orbit due to the acquisition beginning before full opacification.

In such embodiments where the contrast data spans more than a single orbit, reconstruction of the acquired contrast data can be performed for multiple or for different time points. Alternatively, the entire contrast uptake and washout sequence may be reconstructed from the contrast data 140 in multiple volumes, as depicted by the solid and dashed arrows associated with contrast data 140. In such an implementation, arterial phase, venous phase, and other vascular flow distinctions may be observed or leveraged in the reconstruction process. Further, in certain embodiments, acquisition and/or reconstruction of less than a full orbit of contrast data 140 may be performed.

In a further modification to the above-described approach, which may be performed in conjunction with the extension of the contrast data acquisition described above, compound images may be formed. In one such embodiment, the compound images may be formed by creating, at least some view angles, an image from two or more contrast images at that angle. For example, such a contrast image may be formed by picking for each pixel the maximum opacification value from among the corresponding pixels of the two or more contrast images at that view angle. In this manner, it may be possible to generate a representation of the full vessel tree at maximum opacification as opposed to just different phases of opacification.

In an additional modification, the uncoupling of the motion of the support structure (e.g., gantry or C-arm) from data acquisition allows data acquisition to be triggered at any time in the process. That is, activation of the X-ray source and detector can begin at any point when they are being moved, and is not tied to beginning at a certain position or time in a movement cycle. Therefore, the acquisition sequence(s) may be triggered more easily or precisely with the inputs of sensed physiological inputs obtained using a separate device or monitor, such as an electrocardiograph or respiratory monitor. Alternatively, as noted above, acquisition of contrast data may be tied to the observable progress of the contrast within the vasculature (such as using a low acquisition frame rate), as opposed to being based on a best guess of the time to opacification. For example, after contrast is administered, X-ray data may be acquired at a low or reduced frame rate for the purpose of evaluating the progress of the contrast in the vasculature. Based on this low frame rate data, once opacification is sufficient, the frame rate may be increased to the full acquisition frame rate for the prescribed time (e.g., one orbit duration)

In a further modification, and as shown as an alternative embodiment in FIG. 4, before entering into steady-state periodic motion (e.g., during interval 158), a set of additional or augmented mask data 250 may be acquired. During this interval, the motion of the C-arm(s) may not correspond precisely to the motion exhibited during the steady-state periodic motion phase of the examination (i.e., after time 166). For example, larger or smaller tomosynthesis angles may be present in this earlier interval 158. Alternatively, before entering into the periodic orbits at time 166, the C-arm or gantry may sweep up from a lateral position into a PA (Posterior-Anterior) position (or close to it) before entering into periodic tomosynthesis orbits centered about the PA axis.

In such embodiments, more complete data may be acquired for the mask image or construct, that is the 3D mask volume would be of better image quality. In this manner, it may be easier to place subtracted vasculature or structures in the relation to other anatomical features (e.g., bones). Since the subtracted information may be assumed to be more sparse, good image quality may be obtained with fewer projections; i.e., if a reconstruction and visualization of both background (i.e., mask) and structure of interest (i.e., opacified vasculature) is desired, the more complete data (i.e., the data acquired during at least one orbit, plus the augmented data) for the mask (background, including bone and other anatomical structure) ensures better image quality for the background, while the sparseness of the subtracted images enables good image quality of the reconstructed structure of interest from more incomplete data (i.e., fewer projections, as acquired from a single orbit, with the corresponding mask data subtracted). Similarly, in the context of a bi-plane system, the bi-plane data may be used for only the mask data, i.e., the second imager may acquire the mask data 124 while the first image acquires contrast data 140. Alternatively, the lateral beamline may be sampled at a lower frame rate during acquisition of the contrast data 140.

In addition, another modification is to acquire additional mask data 252 after the contrast bolus is washed out. This additional mask data 260 may be acquired using the same steady-state periodic motion as used to acquire mask data 124 and contrast data 140 or using an augmented geometry as discussed with respect to the interval 158. In certain embodiments, additional mask data may be acquired both during interval 158 as well as after contrast washout, with the superior set of additional mask data (e.g., the set that offers the least misalignment for subtraction) being selected for use in processing.

With the preceding in mind, example arrangements of certain X-ray imagers suitable for use with the present approach are discussed in further detail below with respect to FIGS. 1 and 2. In the depicted examples, a first imager is depicted which uses a 2-axis trajectory. While the first image alone may be sufficient for the present approach, in certain embodiments, and as depicted in the figures, a second imager may be provided to acquire additional X-ray projection data, such as over a different limited angular range with respect to the imaged volume. The data from one or both imagers may then be used to create a volumetric image. Both the first and the second imager may be separately and independently controlled so as to be stationary, to move in a linear trajectory, to move in a more complex (e.g., non-linear) trajectory, or to move in a combination of these trajectories at different times.

As discussed herein, in some configurations, a dynamic process (e.g., perfusion) is imaged using the tomosynthesis system. In such implementations, the trajectory may be defined such that the orbit time (i.e., time for one pass through the trajectory) is adapted to the time scale of the observed process. For example, in perfusion imaging, a suitable orbit time may be 3 seconds or less. For higher quality baseline (i.e., mask) data, the data collected before the onset of the dynamic process (e.g., before the injection of contrast media) may include data from an orbit with a larger angular range, and an associated longer orbit time compared to the trajectories used during the dynamic process. In some configurations, the approach may be used to perform DSA (digital subtraction angiography) imaging or comparable techniques. In certain such implementations, projection images are acquired before the injection of contrast (this dataset is usually termed "mask images") and after the start of the contrast injection projection images (i.e., contrast images) are also collected (once or during multiple passes of the trajectory) at essentially the same projection directions, thereby enabling subtraction of the projection images (removing the anatomical background and leaving only the contrast medium, maybe as a function of time) before feeding the images into the reconstruction. Orbit times, tomographic angles, frame rates, etc., may also be adapted/modified during the imaging process. Such adaptations/modifications may be made, for example, in response to physiologic events (e.g., breathing), or other events (tool motion, injection of contrast, operator intervention, etc.). Thus, other physiological monitoring systems (e.g., electro-cardiographs, respiratory monitors, and so forth) may be present to provide physiological data (heart rate, respiration, and so forth) used to prospectively or retroactively gate the image acquisition of contrast injection processes.

While the preceding discussion has focused primarily on vascular imaging, it should be appreciated that the present approach may also be implemented to facilitate navigational and interventional procedures. For example, the present approach may also be employed for tracking interventional tools or devices. In such contexts, digital subtraction between subsequent orbits may be employed to allow for tracking of the progress of a catheter tip, by way of example. In such embodiments, this functionality may be provided after a contrast-based procedure, as discussed above (e.g., DSA), thereby allowing the catheter or other tool to be tracked within the vasculature.

With respect to the above discussion, it should be appreciated that the motion of the imager components is continuous and repeatable (generally in a smooth motion that minimizes mechanical vibration), though the imager components themselves may be operated only periodically (i.e., during acquisition intervals). This is in contrast to current approaches where a temporal delay is introduced mostly due to positioning of the gantry (i.e., the imager components are stopped and repositioned) between the mask and contrast acquisitions when the contrast bolus in introduced. Because the acquisition is continuous and repeatable, the acquisition may be extended to capture the bolus progression (perfusion) through the vasculature and organs of interest. This may be accomplished by continuing the acquisition until the perfusion is complete. Four dimensional (4D) reconstruction processing methods may then be employed to capture 3D samples of the distribution of the contrast bolus in time. In this manner, a record of the perfusion of the contrast over time may be captured and reproduced as opposed to simply reproducing the static vessel tree.

With the preceding discussion in mind, advantages of the present approach include the use of a continuous, periodic gantry motion, which, in addition, is decoupled from the timing of the X-ray exposure (e.g., on-time) as well as from the timing of the contrast administration. This combination enables increased flexibility in the data acquisition, with the following specific advantages: (1) less intrusive 3D acquisition and better patient access (as compared to spin-type acquisitions); (2) greater tolerances on contrast injection timing; (3) continuous data acquisition capability without dead-time; (4) little to no delay between mask and contrast projection acquisition (e.g., allowing acquisition during a single breath-hold), leading to improved registration and therefore improved image quality; (5) short orbit time leading to reduced bolus time and quantity, thereby allowing reduced volume of the contrast medium; (6) repeatability of motion trajectory. By way of comparison, in spin imaging acquisitions using conventional back-and-forth spin acquisition, the trajectory geometries between the spin directions are different, due to different acceleration forces acting on the gantry.

As will be appreciated, technical advantages of the present approach include, but are not limited to, the relaxation of the synchronization required between the acquisition and delivery of the contrast bolus. In addition, the present approach minimizes or eliminates the temporal delay between the "mask" and "contrast" acquisitions by performing continuous data acquisition, enabling the opportunity for improved registration and consequently improved image quality. Lastly, because the acquisition is continuous, the present approach enables synchronization with physiological monitoring equipment, allowing improved or enhanced gating opportunities with respect to the data acquisition or analysis steps.

These technical advantages translate to significant commercial advantages as well. For example, a clinician has the opportunity to perform a 3D DSA acquisition with a manual bolus injection and is not limited to the power injector. In addition, combined mask and contrast data acquisition (due to continuous data acquisition, can be performed in 6 seconds or less, which is an acceptable time for a breath hold in many situations (i.e., both contrast and mask projection data can typically be acquired within a single breath hold). In addition, the brief orbit period translates to a smaller contrast bolus, which may be important for renally impaired patients, or being able to perform multiple 3D acquisitions over the course of a procedure while not exceeding the recommended contrast budget.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An imaging method, comprising:
during an imaging operation, simultaneously moving an X-ray source and an X-ray detector of a tomographic imaging system with respect to a first axis parallel to a longitudinal axis of a patient support surface and a second axis present in a plane perpendicular to the first axis, wherein the motion with respect to the first axis comprises a pendular motion of a support arm over a first limited angular range relative to the first axis, and wherein the motion with respect to the second axis comprises a sliding motion of a C-arm with respect to the support arm over a second limited angular range, wherein the C-arm support the X-ray source and the X-ray detector on opposite sides of the patient support surface; and
acquiring a first projection dataset using the X-ray source and the X-ray detector;
while the X-ray source and the X-ray detector continue to move after acquisition of the first projection dataset, acquiring a second projection dataset; and
reconstructing at least one 3D subtracted image using the first projection dataset and the second projection dataset.

2. The method of claim 1, comprising:
while the X-ray source and the X-ray detector continue to move, starting the acquisition of the second projection dataset at the same time or subsequent to starting to administer a contrast bolus.

3. The method of claim 2, wherein the first projection dataset comprises a mask projection dataset and the second projection dataset comprises a contrast projection dataset.

4. The method of claim 1, comprising:
starting to administer a contrast bolus at or before the start of the acquisition of the first projection dataset;
acquiring the second projection dataset while the X-ray source and the X-ray detector continue to move and after the contrast bolus is washed out of the imaged volume.

5. The method of claim 4, wherein the first projection dataset comprises a contrast projection dataset and the second projection dataset comprises a mask projection dataset.

6. The method of claim 1, wherein the 3D subtracted image depicts a contrast-enhanced object or region with the non-contrast enhanced background subtracted.

7. The method of claim 1, wherein reconstructing at least one 3D subtracted image comprises:
digitally subtracting one of the projection datasets from the other to generate a difference projection dataset; and
synthesizing a volumetric vasculature image using the difference projection dataset.

8. The method of claim 1, wherein reconstructing at least one 3D subtracted image comprises:
generating a contrast volumetric image by reconstructing the contrast projection dataset;
generating a mask volumetric image by reconstructing the mask projection dataset; and
synthesizing a volumetric vasculature image by digitally subtracting the mask volumetric projection image from the contrast volumetric image.

9. The method of claim 1, comprising:
prior to the X-ray source and the X-ray detector undergoing periodic motion, acquiring a third projection dataset;
wherein reconstructing the at least one 3D subtracted image is performed using the first projection dataset, the second projection dataset, and the third projection dataset.

10. The method of claim 1, comprising:
subsequent to the acquisition of the second projection dataset and while the X-ray source and the X-ray detector continue to move after acquisition of the second projection dataset, acquiring a fourth projection dataset;
wherein the second projection dataset is acquired while contrast is present in the imaged volume and the fourth projection dataset is acquired after the contrast has dissipated from the imaged volume.

11. The method of claim 1, wherein the X-ray source is constrained to move on a first side of the imaged volume and the X-ray detector is constrained to move on a second side of the imaged volume.

* * * * *